US00PP37355P2

(12) United States Plant Patent
Layt

(10) Patent No.: US PP37,355 P2
(45) Date of Patent: Mar. 31, 2026

(54) ***LOMANDRA* PLANT NAMED 'LM360'**

(50) Latin Name: *Lomandra longifolia*
Varietal Denomination: LM360

(71) Applicant: Todd Anthony Layt, Richmond (AU)

(72) Inventor: Todd Anthony Layt, Richmond (AU)

( * ) Notice: Subject to any disclaimer, the term of this patent is extended or adjusted under 35 U.S.C. 154(b) by 26 days.

(21) Appl. No.: 18/831,488

(22) Filed: Feb. 21, 2025

(51) Int. Cl.
*A01H 5/00* (2018.01)
*A01H 6/12* (2018.01)

(52) U.S. Cl.
USPC ..... Plt./373

(58) Field of Classification Search
USPC ..... Plt./373
See application file for complete search history.

*Primary Examiner* — Karen M Redden
(74) *Attorney, Agent, or Firm* — Samuel R. McCoy, Jr.

(57) ABSTRACT

'LM360' is a distinctive cultivar of *Lomandra longifolia* which is characterized by a compact and weeping growth habit with fine, soft to the touch, dark green foliage, improved resistance to root and crown rot disease, as well as the uniformity and stability of these characteristics from generation to generation.

3 Drawing Sheets

Latin name of the genus and species: The Latin name of the genus and species of the novel variety disclosed herein is *Lomandra longifolia.*

Variety denomination: The inventive variety of *Lomandra longifolia* disclosed herein has been given the variety denomination 'LM360'.

BACKGROUND OF THE INVENTION

Parentage: 'LM360' is a seedling selection resulting from an open-pollination and seedling selection process carried out by the inventor at his commercial breeding facility in Clarendon, NSW, Australia. In early spring of 2015, an unnamed, fine-bladed, small-statured female *Lomandra longifolia* plant (unpatented) was placed in close proximity to a plurality of unnamed, fine-bladed, small-statured *Lomandra longifolia* male plants (unpatented). These plants were then allowed to openly pollinate. The exact pollen parent is unknown. In early summer of 2015, seed was collected from the female plant. In spring of 2016, said seed was germinated and the resulting seedlings were grown to maturity to observe for traits deemed desirable to commercial production and sales. After two years of observation, several progeny were selected for their combination of compactness, strong plant vigor, and fine leaf texture. These plants were subsequently planted in the ground to assess their resistance to crown and root rotting diseases. In the fall of 2019, one of these plants was selected for its compact size, weeping habit, soft-to-the-touch and dark green foliage, and improved disease resistance when compared to the female parent and all other progeny.

Asexual Reproduction: 'LM360' was first asexually propagated in 2019 by division of the plant's crown in Clarendon, NSW, Australia and has since been asexually reproduced by meristematic tissue culture propagation. The distinctive characteristics of the inventive 'LM380' variety have proven to be stable through five generations and clones so produced maintain the distinguishing characteristics of the original plant.

SUMMARY OF THE INVENTION

'LM360' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'LM360'. These characteristics in combination distinguish 'LM360' as a new and distinct *Lomandra* cultivar:

1. *Lomandra* 'LM360' exhibits a compact, tussock growth habit with weeping foliage; and
2. *Lomandra* 'LM360' exhibits fine-textured, dark green foliage which is soft to the touch; and
3. *Lomandra* 'LM380' exhibits improved resistance to *Phytophthora* crown and root rot disease.

BOTANICAL DESCRIPTION OF THE PLANT

Figure 1:
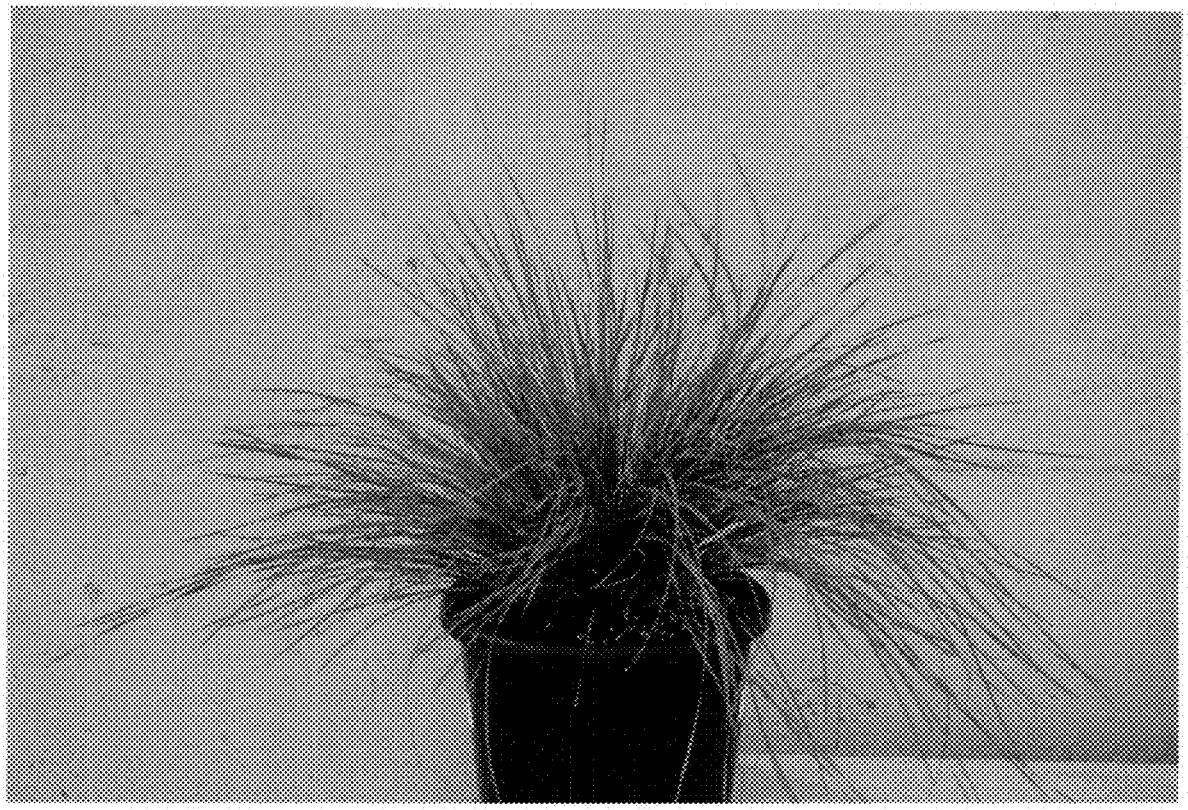
FIG. 1 illustrates, as nearly true as it is reasonably possible to make the same in color photographs of this type, an exemplary 12-month-old 'LM360' plant in a 20 cm nursery pot in Clarendon, New South Wales, Australia.
Figure 2:
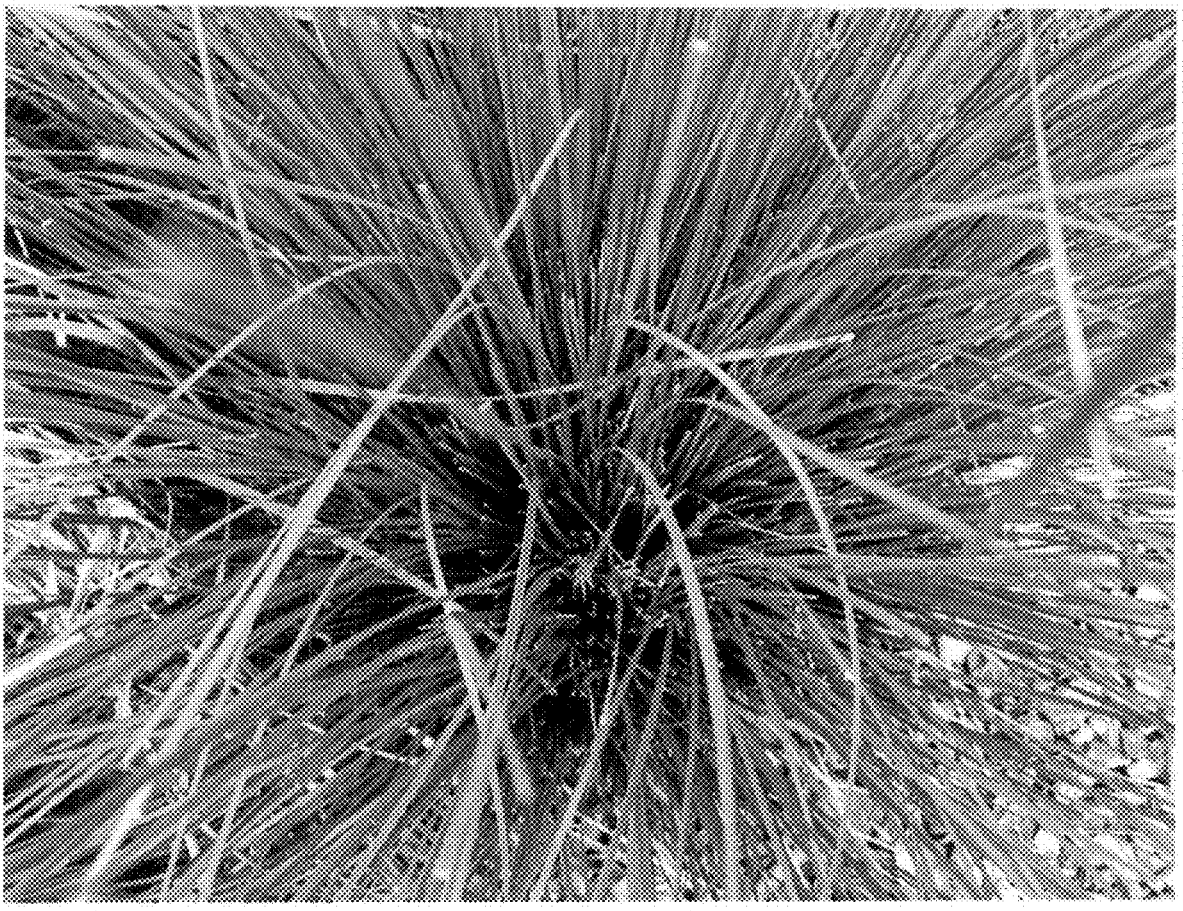
FIG. 2 illustrates, as nearly true as it is reasonably possible to make the same in color photographs of this type, the foliage of 'LM360'.
Figure 3:
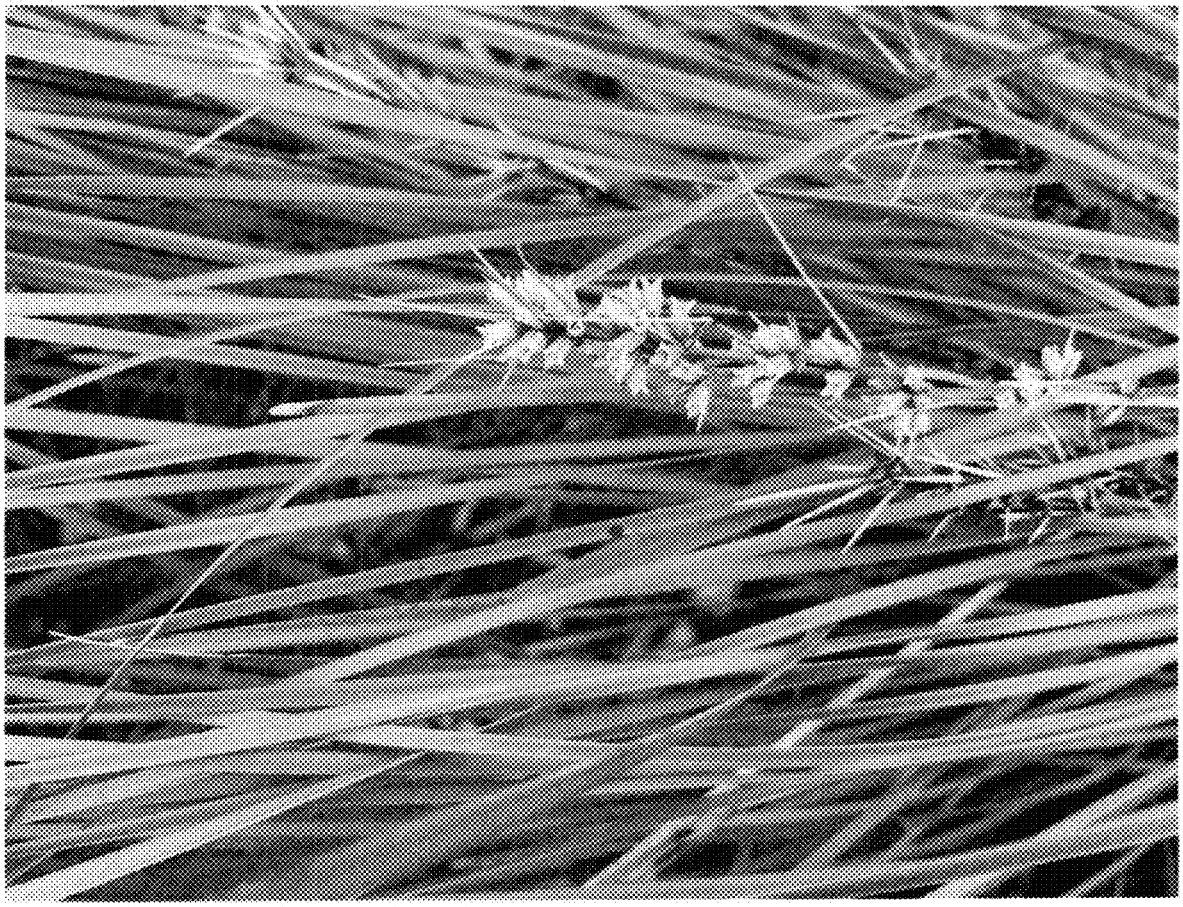
FIG. 3 illustrates, as nearly true as it is reasonably possible to make the same in color photographs of this type, the inflorescence of 'LM360'.

The following is a detailed botanical description of a new and distinct variety of a *Lomandra* ornamental plant known as 'LM360'. Plant observations were made on plants grown in Greeleyville, South Carolina. Unless indicated otherwise, the descriptions disclosed herein are based upon observations made in later October 2024 of 24-month-old 'LM360' plants grown outdoors from rooted cuttings in 250 mm nursery pots filled with soilless potting media, maintained with granular slow-release fertilizer and regularly watered with overhead irrigation. Routine application of herbicide to prevent common pests and diseases.

Those skilled in the art will appreciate that certain characteristics will vary with older or, conversely, younger plants. 'LM360' has not been observed under all possible environmental conditions. Where dimensions, sizes, colors and other characteristics are given, it is to be understood that such characteristics are approximations or averages set forth as accurately as practicable. The phenotype of the variety may vary with variations in the environment such as season, temperature, light intensity, day length, cultural conditions and the like. Color notations are based on *The Royal Horticultural Society Colour Chart*, The Royal Horticultural Society, London, 2001 edition.

A botanical description of 'LM360' and comparisons with the seed parent and several similar variety of common knowledge are provided below.

General plant description:

*Plant habit*.—Grass-like perennial with weeping foliage; rhizomatous plant forming a dense tussock.

*Reproduction*.—Dioecious; female of the species.

*Height*.—46 cm as measured.

*Width*.—75 cm as measured.

*Bloom period*.—Spring.

*Propagation*.—Propagation is accomplished by dividing the crown of the plant or, additionally by way of meristematic tissue culture propagation.

*Crop time*.—Time to initiate rooting is approximately 2 to 3 weeks, depending on the time of year; time to develop a rooted cutting is approximately 12 weeks in a climate-controlled greenhouse. An average crop time in USDA Hardiness Zone 9 is approximately 6 to 9 months to produce a mature and marketable 1-gallon nursery container, beginning with a rooted cutting.

*Environmental tolerances*.—Evergreen in USDA Hardiness Zones 9 through 13 and potentially root hardy in USDA Zone 7; adapt to temperatures ranging from approximately −5 degrees Celsius to 45 degrees Celsius. Shade, drought, and flooding tolerance once established.

*Pest and disease susceptibility or resistance*.—Improved resistance to *Phytophthora* sp. crown and root rot disease.

Roots: Densely rooting; roots are fibrous and distributed evenly throughout the soil profile, from shallow to deep.

Rhizomes: Short, 3 to 4 cm; rhizome color with the leaf sheath removed is greyed-orange, nearest to a combination of RHS 164D and 165D.

Foliage:

*Type*.—Evergreen.

*Shape*.—Linear; grass-like.

*Division*.—Simple.

*Arrangement*.—Whorled around an indistinguishable culm.

*Aspect*.—Arched to weeping.

*Apex*.—Tridentate. The leaf apex may become locally necrotic in response to moisture stress.

*Base*.—Sheathed attachment to the culm.

*Margins*.—Entire.

*Texture, adaxial surface*.—Glabrous; smooth.

*Texture, abaxial surface*.—Glabrous; smooth; glaucous.

*Mature leaf dimensions*.—3 mm wide and 350 mm long, on average. The leaf is generally a uniform width, narrowing only slightly from base to apex.

*Juvenile foliage color, adaxial surface*.—Green, closest to a blend of RHS 143B and 137C.

*Juvenile foliage color, abaxial surface*.—Green, closest to a blend of RHS 143B and 137C.

*Mature foliage color, adaxial surface*.—Yellow-green, closest to RHS 145A at the base of the culm, nearest to RHS 137B and 144A, becoming a darker green to yellow-green, nearest to a combination of RHS 137A and 147A distally; ultimately becoming a lighter green to yellow-green, closest to RHS 137B and 144A.

*Mature foliage color, abaxial surface*.—Yellow-green, closest to RHS 145A at the base of the culm, nearest to RHS 137B and 144A, becoming a darker green to yellow-green, nearest to a combination of RHS 137A and 147A distally; ultimately becoming a lighter green to yellow-green, closest to RHS 137B and 144A.

*Venation*.—Parallel.

*Vein color, adaxial surfaces*.—Indistinguishable from surrounding foliage.

*Vein color, abaxial surfaces*.—Indistinguishable from surrounding foliage.

Inflorescence:

*Type*.—Racemes containing small clusters of male flowers; some flowers are sessile to the rachis while others are borne on pedicels of varying length.

*Natural flowering season*.—Heavy blooming in spring; sporadic in summer and fall.

*Position*.—Racemes positioned within and below the top of the foliar plane.

*Overall dimensions*.—Up to 26 cm long, including the peduncle and rachis.

*Quantity*.—Very floriferous; inflorescences may potentially arise from every shoot.

*Peduncle*.—Dimensions — Up to 16 cm long and 0.2 cm in diameter. Attitude — Semi erect to drooping. Strength — Strong. Texture — Smooth. Color — Yellow-green, nearest to RHS 144B.

*Pedicels*.—Dimensions — Up to 1 cm long and 0.1 cm in diameter. Strength — Strong. Texture — Smooth. Color — Yellow-green, nearest to RHS 145A.

Bud:

*Dimensions*.—Approximately 0.2 cm long and 0.2 cm wide.

*Bud shape*.—Rounded.

*Bud color*.—Yellow, nearest to RHS 10B.

*Rate of bud opening*.—Slow.

Flower:

*Shape*.—Cupuliform; cup-shaped.

*Persistence*.—Non-persistent.

*Aspect*.—Erect.

*Fragrance*.—Non-fragrant.

*Perianth*.—Calyx — Shape — Ovate. Dimensions — Approximately 0.1 mm in diameter. Color — Yellow, nearest to RHS 10B. Texture — Smooth. Sepals — Arrangement — Alternate. Quantity — Three. Margin — Entire. Apex — Aristate. Base — Obtuse. Texture — Smooth. Sepal color, immature, upper surface — Greyed-orange, nearest to RHS 165D. Sepal color, immature, under surface — Greyed-orange, nearest to RHS 165D. Sepal color, mature, upper surface — Greyed-orange, nearest to RHS 165D. Sepal color, mature, under surface — Greyed-orange, nearest to RHS 165D.

*Corolla*.—Arrangement — Alternate; petals unfused. Dimensions — Approximately 0.2 cm in diameter and 0.4 cm deep. Petals — Quantity — Three. Arrangement — Alternate. Dimensions — Approximately 0.2 cm long and 0.1 cm wide. Shape — Ovate. Margin — Entire. Apex — Acute. Base — Obtuse. Texture — Smooth. Color when opening, upper side — Yellow-green, nearest to RHS 150D. Color when opening, under side — Yellow-green, nearest to RHS 150D. Color when fully opened, upper side — Yellow, nearest to RHS 10B. Color when fully opened, under side — Yellow, nearest to RHS 10B.

*Bracts*.—Shape — Needle-shaped. Length — range in length from 0.5 to 1 cm. Apex — Acute. Margin — Entire. Color — Greyed-yellow, nearest to RHS 160D.

Reproduction organs: Not observed.

Seed: Not observed.

COMPARISONS WITH THE PARENT PLANTS

Plants of the new cultivar 'LM360' may be distinguished from the seed parent, and unnamed *Lomandra longifolia* plant, by the characteristics described in Table 1, below.

TABLE 1

| Characteristic | 'LM360' | The seed parent. |
|---|---|---|
| Plant size. | Smaller than the seed parent. | Larger than 'LM360'. |
| Leaf width. | Narrower than the seed parent. | Wider than 'LM360'. |
| Foliage texture. | Softer and more supple than the seed parent. | Stiffer and more rigid than 'LM360'. |
| Resistance to *Phytophthora* infection. | More resistant than the seed parent. | Less resistant than 'LM360'. |

While the exact male parentage is unknown, all possible pollen contributors exhibited a homogenous phenotype. The new cultivar 'LM360' may be distinguished from this population of potential pollen contributors by the characteristics described in Table 2, below.

TABLE 2

| Characteristic | 'LM360' | Potential male parent. |
|---|---|---|
| Plant size. | Smaller than the seed parent. | Larger than 'LM360'. |
| Leaf width. | Narrower than the seed parent. | Wider than 'LM360'. |
| Foliage texture. | Softer and more supple than the seed parent. | Stiffer and more rigid than 'LM360'. |
| Resistance to *Phytophthora* infection. | More resistant than the seed parent. | Less resistant than 'LM360'. |

COMPARISON WITH THE MOST SIMILAR VARIETY KNOWN TO THE INVENTOR

The new cultivar 'LM360' may be distinguished from the most similar variety known to the inventor, *Lomandra longifolia* 'LM300' (U.S. Plant Pat. No. 15,420), by the characteristics described in Table 3, below.

TABLE 3

| Characteristic | 'LM360' | 'LM300' |
|---|---|---|
| Plant size. | Smaller than 'LM300'. | Larger than 'LM360'. |
| Leaf width. | Narrower than the seed parent. | Wider than 'LM360'. |
| Foliage texture. | Softer and more supple than the seed parent. | Stiffer and more rigid than 'LM360'. |
| Resistance to *Phytophthora* infection. | More resistant than the seed parent. | Less resistant than 'LM360'. |

That which is claimed is:

1. A new and distinct variety of *Lomandra longifolia* plant named 'LM360', substantially as described and illustrated herein.

* * * * *